United States Patent [19]

Fakley et al.

[11] Patent Number: 4,775,448

[45] Date of Patent: Oct. 4, 1988

[54] ISOLATION PROCESS

[75] Inventors: Martin E. Fakley, Stockton-on-Tees; Robert J. Lindsay, Bolton, both of England

[73] Assignee: Imperial Chemical Industries PLC, London, England

[21] Appl. No.: 44,299

[22] Filed: Apr. 30, 1987

[30] Foreign Application Priority Data

May 9, 1986 [GB] United Kingdom ................. 8611422

[51] Int. Cl.$^4$ .............................................. B01D 3/40
[52] U.S. Cl. ...................................... 203/62; 568/410
[58] Field of Search ...................... 508/388, 390, 410; 435/148; 203/62

[56] References Cited

U.S. PATENT DOCUMENTS 4,187,356  2/1980  Wagner ................................ 568/414

FOREIGN PATENT DOCUMENTS 0222003   5/1985   Fed. Rep. of Germany ...... 568/388
59-164746 9/1984   Japan ................................... 568/388
59-164745 9/1984   Japan ................................... 568/388
513708   10/1939   United Kingdom ................ 568/388

OTHER PUBLICATIONS

Shigemasa et al., Chem. Abst; vol. 100, #103753k (1984).

Primary Examiner—James H. Reamer
Attorney, Agent, or Firm—Cushman, Darby & Cushman

[57] ABSTRACT

A process of isolating dihydroxyacetone which is a useful intermediate in organic chemistry as well as being a sun-tanning agent. The process comprises passing a reaction mixture containing dihydroxyacetone in an organic solvent through at least one thin film evaporator to distil dihydroxyacetone separately from the solvent.

14 Claims, No Drawings

ISOLATION PROCESS

The present invention relates to a process of purifying a chemical compound and in particular to a process of purifying dihydroxyacetone ($HOCH_2COCH_2OH$).

Dihydroxyacetone is useful as a sun-tanning agent as disclosed in U.S. Pat. No. 2,949,403. In addition dihydroxyacetone is a useful intermediate in many chemical industries, for example in the preparation of pharmaceuticals, dyestuffs, resins and agrochemicals. Accordingly there is a commercial need for dihydroxyacetone in large quantities. At present this is being satisfied by the microbial oxidation of glycerol using for example strains of *Acetobacter suboxydans*. Fermentation methods of producing a chemical compound have drawbacks and a number of studies have been made towards a chemical synthesis of dihydroxyacetone. However none of these has been suggested as operable on a commercial scale. Examples of studies carried out on laboratory scale include those reported by Shigemasa et al, Bull. Chem. Soc. Japan 57, 2761-2767 (1984), Matsumoto et al, JACS 106, 4829-4832 (1984), Matsumoto et al, JCS Chem. Comm. 171 (1983), Matsumoto et al, JOC 50, 603-606 (1985) and Shigemasa et al, J. Carbohydrate Chemistry 2(3), 343-348 (1983).

In general terms, formaldehyde undergoes a condensation reaction in the presence of base to give a mixture of carbohydrates and compounds derived therefrom. This is known as the "formose reaction". The above references discuss the complex nature of the formose reaction and study the effects of various parameters on the reaction, such as varying the temperature, solvent, base, catalyst and/or concentration of reactants. To summarise, certain conditions give higher yields and better selectivity of dihydroxyacetone formation than do other conditions. However, to the best of applicant's knowledge none of the laboratory studies reported in the literature has been commercialised.

This is because of the difficulty of purifying dihydroxyacetone.

The method of purification of dihydroxyacetone from a fermentation broth involves filtering, evaporating under reduced pressure, adding ethanol, filtering, evaporating to a thick syrup, adding acetone, allowing to stand, filtering, evaporating again and crystallising. This procedure is designed for the purification of an aqueous solution of dihydroxyacetone; is inappropriate for the purification of dihydroxyacetone from an organic solution; is long and unwieldly and gives material that is sometimes of relatively low purity.

Matsumoto et al, JACS 106 4829-4832 (1984) describe an isolation procedure that comprises pouring the reaction product in organic solvent into a mixture of water and ether. The water layer is collected, after vigorous shaking, evaporated, dissolved in butanol and subjected to column chromatography on Cellulose Microkristallin (Merck). Other references describe the acetylation of the crude product mixture from the formose reaction with isolation of the acetylated dihydroxyacetone which then is subsequently deacetylated. Clearly neither of these procedures is suitable for a commercial scale isolation of dihydroxyacetone.

A problem of the art is, therefore, to develop a commercially viable isolation procedure for the purification of dihydroxyacetone in organic solvents. The present invention provides a solution to this problem; a solution that gives good recovery yields, high purity, is short and convenient to operate on a commercial scale.

Accordingly the present invention provides a process of isolating dihydroxyacetone from an organic solvent which comprises:

(1) passing said dihydroxyacetone in organic solvent through a thin film evaporator at a temperature and pressure such that dihydroxyacetone distils separately from the solvent, and (2) collecting the distilled dihydroxyacetone.

Typically the dihydroxyacetone in organic solvent is a crude reaction mixture that is optionally filtered prior to passing through the thin film evaporator.

We have found that concentrating such a crude reaction mixture, for example as in normal distillation, results in substantial degradation of dihydroxyacetone. Furthermore we have found that precipitation is not efficient as a number of sugar impurities in the crude reaction mixture precipitate with the dihydroxyacetone, i.e. it is not a selective procedure. In addition we have found that crystallisation of the crude reaction mixture is impracticable because of the number of impurities and the high solubility of dihydroxyacetone and of conventional catalysts. Freeze-drying would not be of benefit as it does not remove the impurities or catalyst, and column chromatography is impracticable on a commercial scale. We have also found that acidic and basic treatment tends to degrade dihydroxyacetone so rendering it difficult to purify and isolate using standard chemical techniques. In view of the foregoing it is significant and advantageous that thin film evaporation enables good isolation and purification to be achieved on direct treatment of the crude reaction mixture.

In addition standard processes of synthesising dihydroxyacetone in an organic solvent comprise the use of a catalyst. Typically the catalyst is of a type that loses activity on contact with water so that most of the separation and isolation procedures of the art are not acceptable if the catalyst is to be reused. It would be at least desirable, and probably necessary, to be able to reuse catalyst when synthesising dihydroxyacetone on a commercial scale. The process of the present invention enables catalyst to be collected and reused, for example in subsequent batch reactions or as part of a continuous process. Preferably sufficient catalyst is recyled to provide at least 50% of the catalyst required for the synthesis of dihydroxyacetone; the remainder being taken off in a purge. In particular sufficient catalyst is recycled to provide at least 75% of the required catalyst. The purge removes catalyst and degradation products to avoid a built-up of such degradation products. The purge can be treated to recover catalyst for possible re-use.

In the process of the present invention the dihydroxyacetone in organic solvent is passed through a thin film evaporator to distil dihydroxyacetone and thus separate it from solvent and residues. Such solvents should be compatible with the conditions used for synthesising dihydroxyacetone.

The solvent can have a higher boiling-point than that of dihydroxyacetone so that dihydroxyacetone distils first and separately from the solvent. This is achieved by having the thin film evaporator at a certain temperature and pressure dependent on the characteristics of the solvent. The solvent can be subsequently distilled, if desired, either; in a second region of the evaporator where the temperature is higher and/or the pressure is lower; or by passing the solvent and residues through a second thin film evaporator with a temperature and pressure such that the solvent is distilled. The residues are collected in conventional manner and, if desired, can be reused as they comprise mainly catalyst. In an alternative the solvent, and residues can be reused without distillation of the solvent, if pure enough, in the synthesis of further dihydroxyacetone. An example of a solvent having a boiling point higher than dihydroxyacetone is polyethylene glycol.

The solvent can have a lower boiling-point than that of dihydroxyacetone so that the solvent distils first and separately from dihydroxyacetone. The dihydroxyacetone is subsequently distilled either; in a second region of the evaporator where the temperature is higher and/or the pressure is lower; or by passing the dihydroxyacetone and residues through a second thin film evaporator having an appropriate temperature and pressure. In these embodiments it is important that the contact time of dihydroxyacetone in the second region of the evaporator or in the second thin film evaporator is sufficiently brief so that there is no substantial degradation of dihydroxyacetone. For example at a feed rate of 106 g.hr$^{-1}$ (dihydroxyacetone crude reaction mixture with solvent already distilled), at a wall temperature of about 105° C. and at a vacuum of about 0.1 –0.2 mm Hg and wherein the film thickness is about 0.1 mm, the contact time is up to or about 60 seconds. The residues can be collected in conventional manner and reused if desired. Examples of solvents having boiling-points lower than dihydroxyacetone include dimethylformamide, 1,4-dioxan, dimethylsulphoxide and acetonitrile.

In a preferred aspect of this invention dimethylformamide is used as the solvent as it is a suitable reaction solvent for the synthesis of dihydroxyacetone and it has properties that enable it to be readily separated from dihydroxyacetone, dimethylformamide distils at about 70° C./20 mm for example and dihydroxyacetone distils at about at 90°–115° C./0.1–0.5 mm Hg for example. Conveniently two thin film evaporators are used; the crude reaction mixture is passed through the first at a temperature and pressure to distil dimethylformamide, the dihydroxyacetone and residues are then passed through the second at a temperature and pressure to distil dihydroxyacetone and the residues, mainly catalyst, are collected from the second evaporator and, if desired, are recycled, after the removal of a purge as previously discussed.

Dihydroxyacetone is obtained from the process of this invention in substantially pure form, generally as a mixture of a solid and syrup. This material can be used, without further purification, in many of the applications and uses of dihydroxyacetone. If necessary this material can be purified even further in conventional manner, for example by crystallisation. Crystallisation is facile as the material distilled from the thin film evaporator is of substantial purity.

As stated hereinabove, generally the dihydroxyacetone in an organic solvent to be passed through the thin film evaporator is the crude reaction mixture of a dihydroxyacetone synthesis. The nature of the reaction that leads to the crude reaction mixture is not critical to the present invention but preferably the reaction provides a crude reaction mixture wherein the dihydroxyacetone is reasonably pure as this facilitates the thin film evaporation procedure.

Accordingly in a preferred aspect the present invention provides a process comprising:
(a) heating source of formaldehyde in an organic solvent in the presence of a base and a catalyst until substantial completion of the reaction, and subsequently
(b) passing the reaction mixture down a thin film evaporator at a temperature and pressure such that the dihydroxyacetone distils separately from the solvent, and
(c) collecting the distilled dihydroxyacetone.

Convenient organic solvents include those mentioned specifically above, in particular dimethylformamide, dimethyl sulphoxide, and 1,4-dioxan are preferred.

The formaldehyde may be introduced into the reaction mixture in any convenient form, for example as paraformaldehyde or as formaldehyde gas.

Suitably the reaction is conducted under anhydrous conditions, for example under nitrogen gas using anhydrous reagents and is conducted at an elevated temperature in the range 30° to 100° C., more suitably in the range 50° to 80° C.

Suitable bases and catalysts include those specifically mentioned in the literature referred to hereinabove. For example suitable bases are triethylamine, trioctylamine, quinuclidine, imidazole and ethyldi-isopropylamine.

Suitable catalysts are those of the thiazolium type, for example
3-butylthiazolium bromide,
3-methylbenzothiazolium iodide,
3-ethylbenzothiazolium bromide,
3-isopropylbenzothiazolium bromide,
3-butylbenzothiazolium bromide,
3-ethylbenzothiazolium iodide,
3-benzyl-5-(2-hydroxyethyl)-4-methylthiazolium chloride,
thiamine hydrochloride, and
3,4-dimethylthiazolium methasulphate.

The present invention is illustrated by the following Example.

EXAMPLE 1

To a reaction vessel is charged anhydrous dimethylformamide (105 parts by weight). This is heated to 60° C. under a nitrogen atmosphere. 3,4-Dimethylthiazolium methasulphate (1.35 parts) (prepared by stirring 4-methylthiazole with dimethyl sulphate at 60° C. in toluene, isolating and drying) is added over 10 minutes. Subsequently paraformaldehyde (2 parts) was added, followed by triethylamine (0.6 parts). The mixture was agitated at 60° C. under nitrogen. Further aliquots of paraformaldehyde (2 parts each) were added as a slurry in dimethylformamide after 2, 4, 6 and 8 hours. The mixture was agitated under nitrogen, at 60° C., for a further 5 hours, cooled to 20°–25° C. and discharged to a container through a small screening filter to give a crude reaction mixture of dihydroxyacetone in dimethylformamide.

A portion of this crude reaction mixture was passed down a thin film evaporator* at 70° C. and 20 mm Hg. This removed almost all (95%) of the dimethylformamide by distillation. The residue including dihydroxyacetone was collected and passed down a second thin film evaporator* at 100° C. and 0.2 mm Hg. Dihydroxyacetone (about 80%) distilled and was collected as a solid/syrup material. The residue from the second thin film evaporation procedure, containing catalyst and about 20% of the dihydroxyacetone originally present in the crude reaction mixture, was collected for possible reuse.

*The thin film evaporators were Leybold Heraeus KDL 4 evaporators with 4.3 dm² of wiped surface, and the vacuum pump incorporated a condenser and a vacuum trap.

The purity of the solid/syrup dihydroxyacetone was determined as 97% according to gas liquid chromatography on the trimethylsilylated oxime derivative. See the analytical method of Matsumoto et al., JACS 106, 4829–4832 (1984)..

EXAMPLES 2–10

In a manner similar to that of Example 1, a crude reaction mixture of dihydroxyacetone in dimethylformamide was obtained. This was passed down a first thin film evaporator, as in Example 1, at 70° C./20 mm Hg to remove dimethylformamide. The residue was then passed down a second thin film evaporator, as in Example 1, under a variety of conditions.

| Example | Temp. (°C.) | Pressure (mm Hg) | Feed rate (ghr⁻¹) | Recovery of dihydroxyacetone feed (%) |
| --- | --- | --- | --- | --- |
| 2 | 90 | 0.1–0.2 | 160 | 26.4 |
| 3 | 90 | 0.1–0.2 | 106 | 47.5 |
| 4 | 100 | 0.1–0.2 | 110 | 81.3 |
| 5 | 105 | 0.1–0.2 | 90 | 84.2 |
| 6 | 105 | 0.1–0.2 | 228 | 43.1 |
| 7 | 105 | ~1 | 105 | 70.9 |
| 8 | 110 | 0.1–0.2 | 96 | 59.9 |
| 9 | 110 | 0.1–0.2 | 285 | 48.9 |
| 10 | 114 | 0.1–0.2 | 136 | 74.7 |

According to the method of Matsumoto, the purity values of the recovered dihydroxyacetone were in the range 73–96%.

In all cases the dihydroxyacetone not recovered by distillation could be recycled, after a purge had been taken out, to the reaction vessel in which dihydroxyacetone is synthesised.

We claim:

1. A process of isolating dihydroxyacetone from an organic solvent which comprises:
   (i) passing said dihydroxyacetone in an organic solvent through a thin film evaporator at a temperature and pressure such that dihydroxyacetone distils separately from the solvent, and
   (ii) collecting the distilled dihydroxyacetone.

2. A process according to claim 1 which comprises:
   (i) passing through a thin film evaporator dihydroxyacetone in an organic solvent, said solvent having a boiling-point lower than that of dihydroxyacetone,
   (ii) maintaining, in a first region of said evaporator, the temperature and pressure such that the organic solvent distils,
   (iii) maintaining, in a second region of said evaporator, the temperature and pressure such that dihydroxyacetone distils to provide a dihydroxyacetone distillate, and
   (iv) collecting said dihydroxyacetone distillate.

3. A process according to claim 1 which comprises:
   (i) passing through at least two thin film evaporators dihydroxyacetone in an organic solvent, said solvent having a boiling-point lower than that of dihydroxyacetone,
   (ii) maintaining, in a first thin film evaporator, the temperature and pressure such that the organic solvent distils,
   (iii) maintaining, in a second thin film evaporator, the temperature and pressure such that dihydroxyacetone distils to provide a dihydroxyacetone distillate, and
   (iv) collecting said distillate.

4. A process according to claim 3 which further comprises collecting the solvent distillate and recycling said distillate to a reaction mixture in which a source of formaldehyde in said solvent is heated in the presence of a base and a catalyst to provide a solution of dihydroxyacetone in said organic solvent.

5. A process according to claim 4 wherein the recycled distillate provides at least 75% of the organic solvent in which the source of formaldehyde is heated.

6. A process according to claim 5 wherein the recycled distillate provides at least 90% of the organic solvent in which the source of formaldehyde is heated.

7. A process according to claim 3 which further comprises collecting the non-distilled residues and recycling said residues to provide at least 50% of the catalyst in the presence of which the source of formaldehyde is heated.

8. A process according to claim 7 wherein said residues provide at least 75% of the catalyst in the presence of which the source of formaldehyde is heated.

9. A process according to claim 3 wherein the solvent comprises dimethylformamide.

10. A process according to claim 9 wherein the temperature and pressure of the first thin film evaporator, or first region of the evaporator, are about 70° C. and 20 mm Hg respectively, and the temperature and pressure of the second thin film evaporator, or second region of the evaporator, are in the ranges 90°–115° C. and 0.1–0.5 mm Hg respectively.

11. A process according to claim 1 which comprises:
    (i) passing through a thin film evaporator dihydroxyacetone in an organic solvent, said solvent having a boiling-point higher than that of dihydroxyacetone,
    (ii) maintaining, in a first region of said evaporator, the temperature and pressure such that the dihydroxyacetone distils to provide a dihydroxyacetone distillate, and
    (iii) collecting said distillate.

12. A process according to claim 11 which further comprises recycling the non-distilled residue to a reaction mixture in which a source of formaldehyde in said organic solvent is heated in the presence of a base and a catalyst to provide a solution of dihydroxyacetone in said organic solvent.

13. A process of preparing dihydroxyacetone which comprises:
    (i) heating a source of formaldehyde in an organic solvent, said solvent having a boiling-point lower than that of dihydroxyacetone, in the presence of a base and a catalyst until substantial completion of the reaction,
    (ii) passing the reaction mixture through at least two thin film evaporators,
    (iii) maintaining, in a first thin film evaporator, the temperature and pressure such that the organic solvent distils,
    (iv) maintaining, in a second thin film evaporator, the temperature and pressure such that dihydroxyacetone distils to provide a dihydroxyacetone distillate, and
    (v) collecting said distillate.

14. The process of claim 1 wherein the dihydroxyacetone is distilled with a purity of from 73–97%.

* * * * *